United States Patent [19]

Bartoli

[11] 4,225,668
[45] Sep. 30, 1980

[54] BLADE ENDO-OSSEOUS APPARATUS FOR DENTAL PLATES, AND FIXING METHOD THEREFOR

[76] Inventor: Gian V. Bartoli, Milan, Italy

[21] Appl. No.: 967,702

[22] Filed: Dec. 8, 1978

[30] Foreign Application Priority Data

Dec. 16, 1977 [IT] Italy .................................. 30857 A/77

[51] Int. Cl.³ .............................................. A61C 13/00
[52] U.S. Cl. .................................................... 433/176
[58] Field of Search ......................... 32/10 A; 433/176

[56] References Cited

U.S. PATENT DOCUMENTS

| | | | |
|---|---|---|---|
| 1,140,538 | 5/1915 | Skinner | 32/10 A |
| 2,836,890 | 6/1958 | Sibuis | 32/10 A |
| 3,414,975 | 12/1968 | Small | 32/2 |
| 3,514,858 | 6/1970 | Silverman | 32/2 |
| 3,748,739 | 7/1973 | Thibert | 32/10 A |
| 3,837,080 | 9/1974 | Pasqualini | 32/10 A |

Primary Examiner—Robert Peshock
Attorney, Agent, or Firm—Bucknam and Archer

[57] ABSTRACT

An improved endo-osseous apparatus for dental plates is described which comprises a series of blades for the anchoring to the osseous tissue of the gums. The upper portion of each anchoring blade is formed by a projecting threaded pin of small diameter, provided with a movable or fixed cap or bush and with an internally threaded hollow element adapted to be screwed onto the pin. A ferula is provided with through holes, for insertion of the pins. The anchoring blades are fixed to the ferula by means of threaded hollow elements or knurled nuts which are screwed to the pin. The threaded hollow element may be a frustum conical cap, with the end zone flap-enlarged and having the same diameter as the cap or bush. The ferula may be provided with projections, each projection having a frustum-conical shape, the projections located at the two hollow ends of the ferula being hollow and internally threaded, thus allowing for the prosthesis to be fixed by screws passing through the corresponding holes of the prosthesis teeth and screwed in the projections. A temporary ferula is fixed into the projecting pins, and a temporary prosthesis is fixed onto the temporary ferula. After perfect cicatrization has occurred, the temporary prosthesis and ferula are removed, the final ferula is fixed by means of the internally threaded hollow elements, and the final prosthesis provided with suitable through holes is fixed.

11 Claims, 11 Drawing Figures

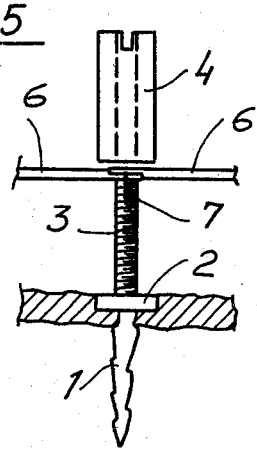
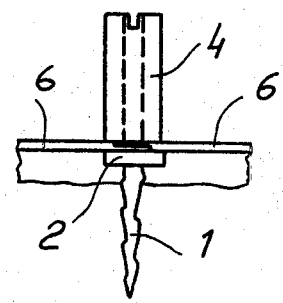
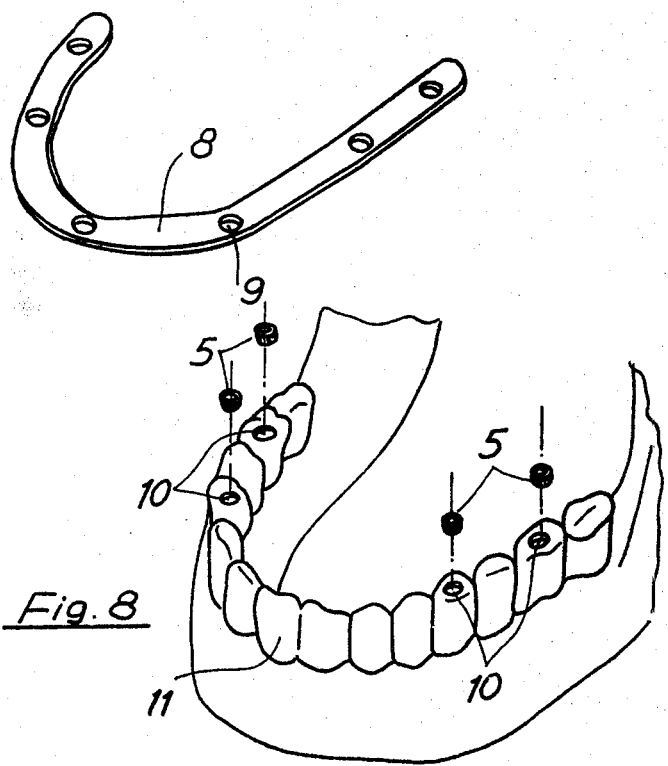

BLADE ENDO-OSSEOUS APPARATUS FOR DENTAL PLATES, AND FIXING METHOD THEREFOR

The present invention relates to an improved blade endo-osseous apparatus, for dental plates, and to the method for applying of fixing said apparatus.

As it is known, the blade implantation allows for dental prostheses fixedly anchored to the osseous tissue.

This type of fixing, while providing optimal results from the point of view of a very good stability of the prostheses, presents some drawbacks as any subsequent modifications reveal necessary.

In fact, in this case, a new radical operation has to be carried out onto the osseous tissue, which involves the extraction of the blades therein embedded and the subsequent reinserting of said blades.

Obviously these are rather difficult and painful operations and cause futher sufferings to the patient.

Accordingly the main object of the present invention is to provide a blade endo-osseous apparatus, for dental plates, free of the drawback discussed hereinabove.

More specifically, the object of the present invention is to provide a blade endo-osseous apparatus, for dental plates, effective to allow for the outer structure of the prostheses to be easily removed and subsequently replaced without causing traumas and sufferings to the patient.

The Applicant has found that this object is achieved by an improved endo-osseous apparatus for dental plates comprising anchoring blades, each blade having the upper portion thereof, which has to project from the osseous plane and soft parts, formed by a small diameter threaded pin provided with a cap and with an innerly threaded hollow cylindrical element effective to be screwed onto said pin, and further comprising connecting means provided with a plurality of through orifices for insertion of the threaded pins of the anchoring blades to which is fixed the prosthesis. The cap may be fixed or movable.

The connecting means may be provided with projections effective to stabilize the position of the dental prosthesis, or this function may be carried out by the threaded cylindrical movable elements of each anchoring blade.

The anchoring of the dental prosthesis is obtained by screws passing through the prosthesis teeth and fixed in suitable threaded projections of the connecting means. The prosthesis may be fixed directly to the threaded pins of the blades.

In order to stabilize the anchoring blades during the cicatrization of the gums, it is practically preferred to firstly use temporary connecting means which may be subsequently removed, after the cicatrization, to be replaced by the final connecting means.

This temporary or provisional connecting means may be either formed by a single piece or by a plurality of small rods, suitably shaped and effective to be bent, the small rods being provided at the ends thereof with suitable orifices for the anchoring of the threaded pins and for the mutual connecting to one another.

In order to better comprise the constructive and operative characteristics of the endo-osseous apparatus according to the present invention, the apparatus will be thereinbelow described with reference to the figures of the accompanying drawings illustrating several preferred exemplary non limitative embodiments thereof, where;

FIGS. 5 and 6 are detail views illustrating the fixing of superimposed rod pairs;

FIG. 7 is a schematic view illustrating a particular shape for the final connecting means;

FIG. 8 is a top schematic view illustrating the final prosthesis and the fixing thereof by the connecting means shown in FIG. 7;

FIG. 9 illustrates another embodiment of the hollow and threaded cylindrical element the blade shown in FIG. 1 may be provided with;

Referring particularly to the FIGS. 1 to 8, the improved endo-osseous apparatus for dental prostheses according to the present invention, comprises a series of blades for the anchoring to the gum osseous tissue, each blade having the lower portion 1 thereof, to be embedded in the bone, which is of known shape, whereas the projecting portion is formed, for a third of the height thereof, by a cap 2 and, for the remaining two thirds, by a small diameter threaded pin 3. The caps 2, which have a wider cylindrical upper portion, may be fixed or, in a preferred way, movable by screwing, thereby correcting possible level differences between the three upper surfaces thereof.

Figure 1:
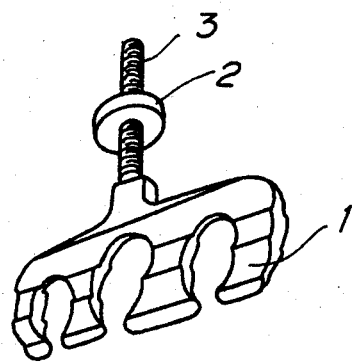
FIG. 1 is a front schematic view of an anchoring blade.
Figure 2:
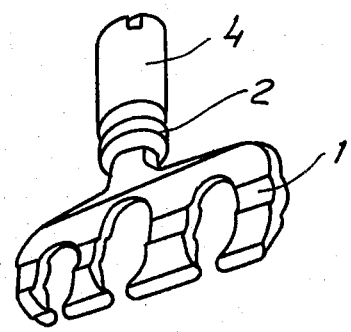
FIGS. 2 and 3 illustrate the blade of FIG. 1 respectively provided with a cylindrical element, threaded in the interior thereof, and with a nut.
Figure 3:
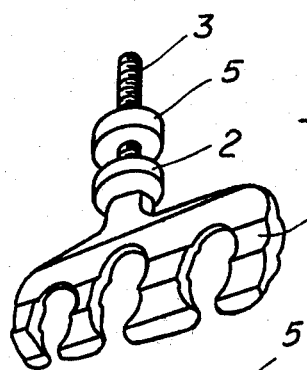

Onto the pin 3 is screwed a hollow and threaded element 4 (FIG. 2) or knurled nut 5 (FIG. 3).

Figure 9:
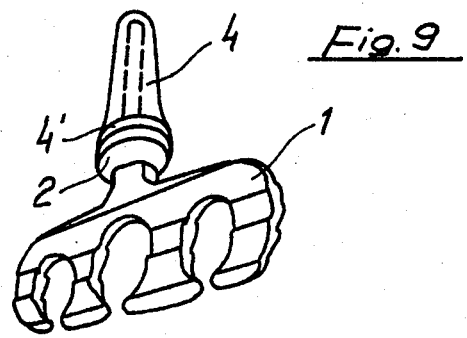

The threaded hollow element 4 may be formed by a cylinder having a notched head (FIG. 2) or it may consist of a frustum coneshaped cap with the end zone 4' thereof flap enlarged and having a diameter equal to that of said cap 2 (FIG. 9).

The element 4 as well as the anchoring blade are preferably made of titanium, but is should be pointed out that other materials and metal alloys, such as gold or "Pernabond", may be used, since element 4 is not provided for contacting the osseous tissue.

Upon fixing the lower portion 1 of each anchoring blade into the osseous tissue by means of any known type of operation, from the bone surface and the gum tissue project the threaded pins 3. Onto each said pin is screwed a cap 2 in such a way that this latter is held housed within the soft part of the gum.

Figure 4:
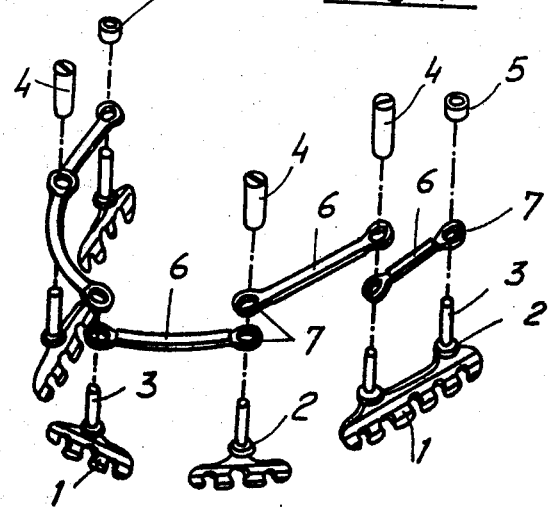
FIG. 4 illustrates a schematic view of the temporary or provisional connecting means in the case in which this latter is formed by a plurality of connecting rods.

The several pins 3 are connected to one another by a connecting means which may be either integral and provided with orifices for the insertion of pins 3, of the type of the final ferula 8 illustrated in FIG. 7, or formed by a plurality of stabilizing small rods 6 having flattened and bored ends 7 and made of a metal material such as gold or "Pernabond", preferably of titanium (see FIG. 4).

The small rods 6 have different lengths depending on the distance of the pins 3, they are bent to follow the gum outline, and may be bent in such a way as to fit to the single portions of each tooth-shaped part.

This connecting small rods 6, which form the temporary connecting means, are precisely fixed at contact with the caps 2 by screwing onto each pin 3 the threaded elements 4 and knurled nuts 5.

Onto the thus fixed temporary connecting means is placed a resin temporary or provisional prosthesis, already previously prepared.

The provisional prosthesis is maintained in situ until a perfect cicatrization has occurred, and then the temporary prosthesis and connecting means are removed, by removing the holding elements 4 and 5, and are also removed the suture points.

Then, is introduced the final ferula 8 which, to this end, is provided with a plurality of through holes 9 into which the threaded pins 3 of the blades are inserted.

Also this final connecting means is preferably made of titanium.

The final connecting means 8 is fixed to the blades by the knurled nuts 5 or the hollow threaded cylindrical elements 4, which may be of different heigth thereby leaving free the end upper portion of the pins 3. In particulary, is left free the upper end portion of the pin 3 corresponding to the teeth of the final prosthesis 11, provided with orifices 10.

In this manner, the anchoring of the prosthesis 11 to the pins 3 is carried out by the knurled nuts 5 screwed onto the pins at the holes 10.

The stabilization of the prosthesis 11 is assured by the presence of the hollow cylindrical elements 4 rigid with the blades 1 and projecting from the connecting means 8.

Figure 10:
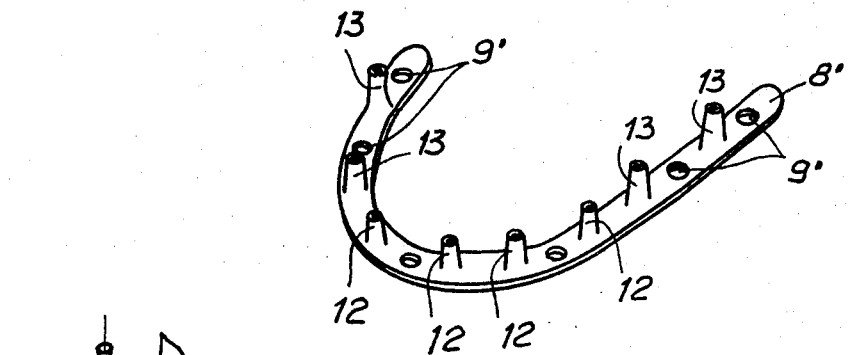
FIG. 10 illustrates a top schematic view of another embodiment of the final connecting means.
Figure 11:
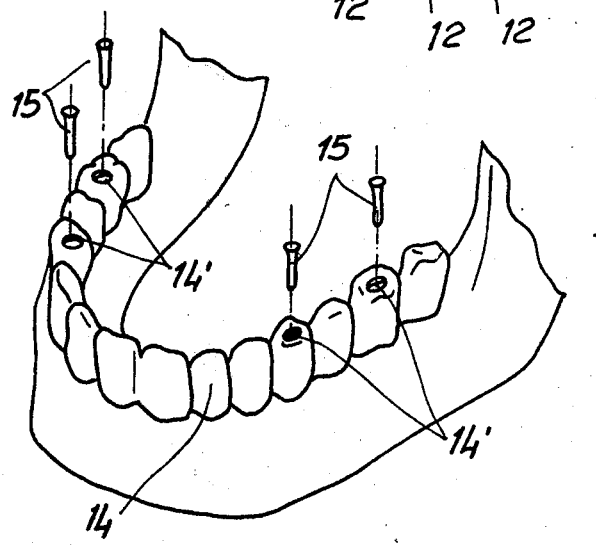
FIG. 11 illustrates a top schematic view of the final prosthesis and the fixing thereof by the connecting means shown in FIG. 10.

In FIGS. 9, 10 and 11 is illustrated another embodiment of the endo-osseous apparatus for prostheses according to the present invention.

As it is shown, the threaded hollow element 4 has the shape of a frustum conical cap with the underlying zone 4 flap-enlarged and having a diameter equal to that of the cap 2. Moreover, the final connecting means 8' is provided with holes 9 into which are inserted the threaded pins 3 of the blades, and projections 12 and 13, each projection having a frustum conical section. In particular, the projections 12 act for supporting and stabilizing the prosthesis 14 onto the ferula 8', whereas the projections 13, located at the two ends of the ferula, are hollow and innerly threaded. These projections 13 allow for the prosthesis 14 to be fixed onto the connecting means 8' by means of screws 15 passing through holes 14', the holes 14' being formed in some end prosthesis teeth, and screwed to the threaded projections 13.

From the above description and the observation of the several figures of the accompanying drawings are self evident the functionality and advantages characterizing the endo-osseous apparatus for prostheses according to the present invention.

Modifications, variations and changes may be carried out in the embodiments illustrated in the accompanying drawings, without departing from the spirit and scope of the invention.

What is claimed is:

1. An endo-osseous apparatus for the teeth of the prosthesis comprising:
   a plurality of blades for the anchoring to the osseous tissue of the gums;
   a threaded pin projecting from each anchoring blade;
   a cap placed onto each said pin, said cap being held housed within the gums;
   a first connecting means comprising rods between the adjacent blades to join the adjacent blades provided with orifices for the insertion of said pins;
   second means for fixing said first connecting means to the blades and for stabilizing the prosthesis, engageable with each pin, said second means comprising a hollow threaded element; and
   third means for screwing the prothesis onto said second supporting means.

2. The apparatus according to claim 1 wherein the cap is fixed.

3. The apparatus according to claim 1 wherein each cap is screwed onto each said pin.

4. An apparatus according to claim 1 wherein the threaded hollow element is cylindrical and has a notched head.

5. An apparatus according to claim 1 wherein the threaded hollow element is a frustum conical cap, with the end flap-enlarged and having the same diameter as said cap.

6. An apparatus according to claim 1 wherein the threaded hollow element is a knurled nut.

7. An apparatus according to claim 1 wherein the threaded hollow element is made of titanium.

8. An apparatus according to claim 6 wherein the upper end portion of each of the threaded pins, located at the end of said first connecting means is left free, the teeth of the prosthesis have orifices, and onto each free portion is screwed said knurled nut which passes through said orifices of the teeth at said free end of the threaded pins for fastening said prosthesis.

9. An apparatus according to claim 8 wherein the first connecting means are provided with projections, each said projection having a frustum-conical shape, the projections located at the two hollow ends of said first connecting means being hollow and innerly threaded, and screws pass through the orifices of the prosthesis teeth and holding said teeth in said projections.

10. An apparatus according to claim 9 wherein said first connecting means is made of titanium.

11. The apparatus according to claim 1 wherein said first connecting means comprise a plurality of curved small rods, having different lengths, having flattened ends, said ends being provided with orifices, said projecting pins being inserted through said orifices.

* * * * *